(12) United States Patent
Yamada et al.

(10) Patent No.: US 11,351,279 B2
(45) Date of Patent: Jun. 7, 2022

(54) HYPHAE INHIBITION APPARATUS AND HYPHAE INHIBITION METHOD

(71) Applicant: PANASONIC INTELLECTUAL PROPERTY MANAGEMENT CO., LTD., Osaka (JP)

(72) Inventors: Makoto Yamada, Osaka (JP); Shinichi Aoki, Osaka (JP)

(73) Assignee: PANASONIC INTELLECTUAL PROPERTY MANAGEMENT CO., LTD, Osaka (JP)

( * ) Notice: Subject to any disclaimer, the term of this patent is extended or adjusted under 35 U.S.C. 154(b) by 403 days.

(21) Appl. No.: 16/570,064

(22) Filed: Sep. 13, 2019

(65) Prior Publication Data

US 2020/0093944 A1 Mar. 26, 2020

(30) Foreign Application Priority Data

Sep. 21, 2018 (JP) .............................. JP2018-176881

(51) Int. Cl.
*A61L 2/00* (2006.01)
*G01N 23/00* (2006.01)
(Continued)

(52) U.S. Cl.
CPC ................ *A61L 2/10* (2013.01); *H05B 45/00* (2020.01); *H05B 47/16* (2020.01)

(58) Field of Classification Search
CPC ...... A61L 2/0047; A61L 2/0052; A61L 2/084; A61L 2/10; A61L 2202/20
(Continued)

(56) References Cited

U.S. PATENT DOCUMENTS

2011/0163246 A1 7/2011 Ishiwata et al.
2018/0043044 A1 2/2018 Hachiya et al.

FOREIGN PATENT DOCUMENTS

CN 101909425 A 12/2010
JP 2006-200358 A 8/2006
(Continued)

OTHER PUBLICATIONS

Office Action, dated Dec. 14, 2020, for the corresponding Chinese Patent Application No. 201910821327.8, with English Language Search Report.

(Continued)

*Primary Examiner* — Monzer R Chorbaji
(74) *Attorney, Agent, or Firm* — Greenblum & Bernstein, P.L.C.

(57) ABSTRACT

A hyphae inhibition apparatus irradiates an organism having hyphae with light to inhibit growth of the hyphae. The hyphae inhibition apparatus includes a first light source generator, including at least one of a violet light source that emits light having a peak wavelength in a range of from 380 nm to 410 nm, inclusive, or a UVB light source that emits light having a peak wavelength in a range of from at least 280 nm to below 350 nm. The hyphae inhibition apparatus also includes a second light source generator, including at least one of a blue light source that emits light having a peak wavelength in a range of from at least 350 nm to below 380 nm or a UVA light source that emits light having a peak wavelength in a range of from 415 nm to 480 nm, inclusive.

10 Claims, 6 Drawing Sheets

(51) Int. Cl.
  *A61N 5/00*   (2006.01)
  *A61L 2/10*   (2006.01)
  *H05B 45/00*  (2022.01)
  *H05B 47/16*  (2020.01)
(58) Field of Classification Search
  USPC .................. 422/22, 24; 250/455.11, 492.1
  See application file for complete search history.

(56) References Cited

FOREIGN PATENT DOCUMENTS

| JP | WO 2009/081272 | * | 7/2009 | ........... A61L 2/0047 |
| JP | 2012-183014 A | | 9/2012 | |
| JP | 2018-027291 A | | 2/2018 | |
| WO | 2009/081272 A2 | | 7/2009 | |
| WO | 2010-047277 A1 | | 4/2010 | |

OTHER PUBLICATIONS

Japan Office Action, dated Jan. 11, 2022 by the Japan Patent Office (JPO), for the corresponding Japanese Patent Application No. 2018-176881.

* cited by examiner

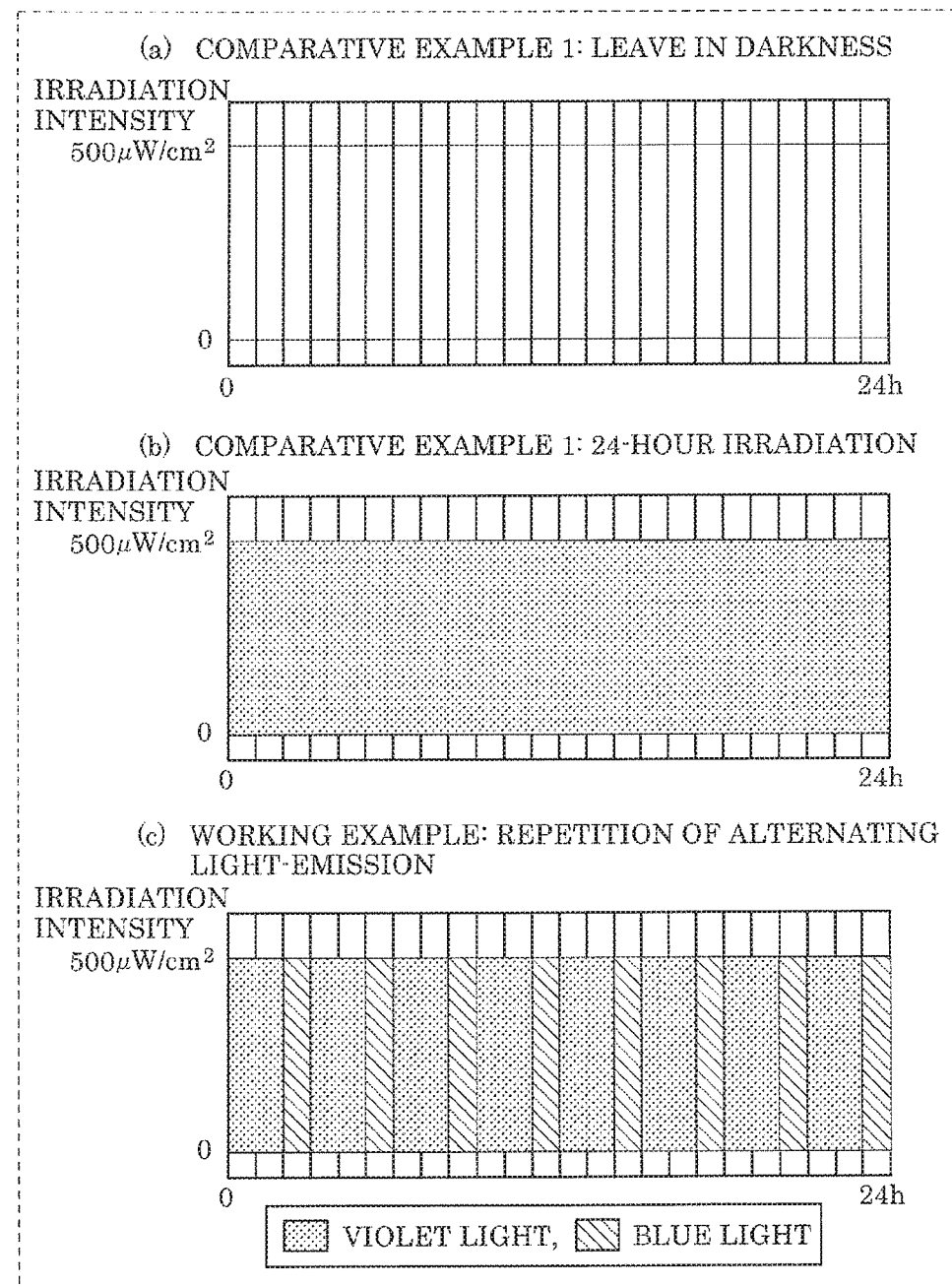

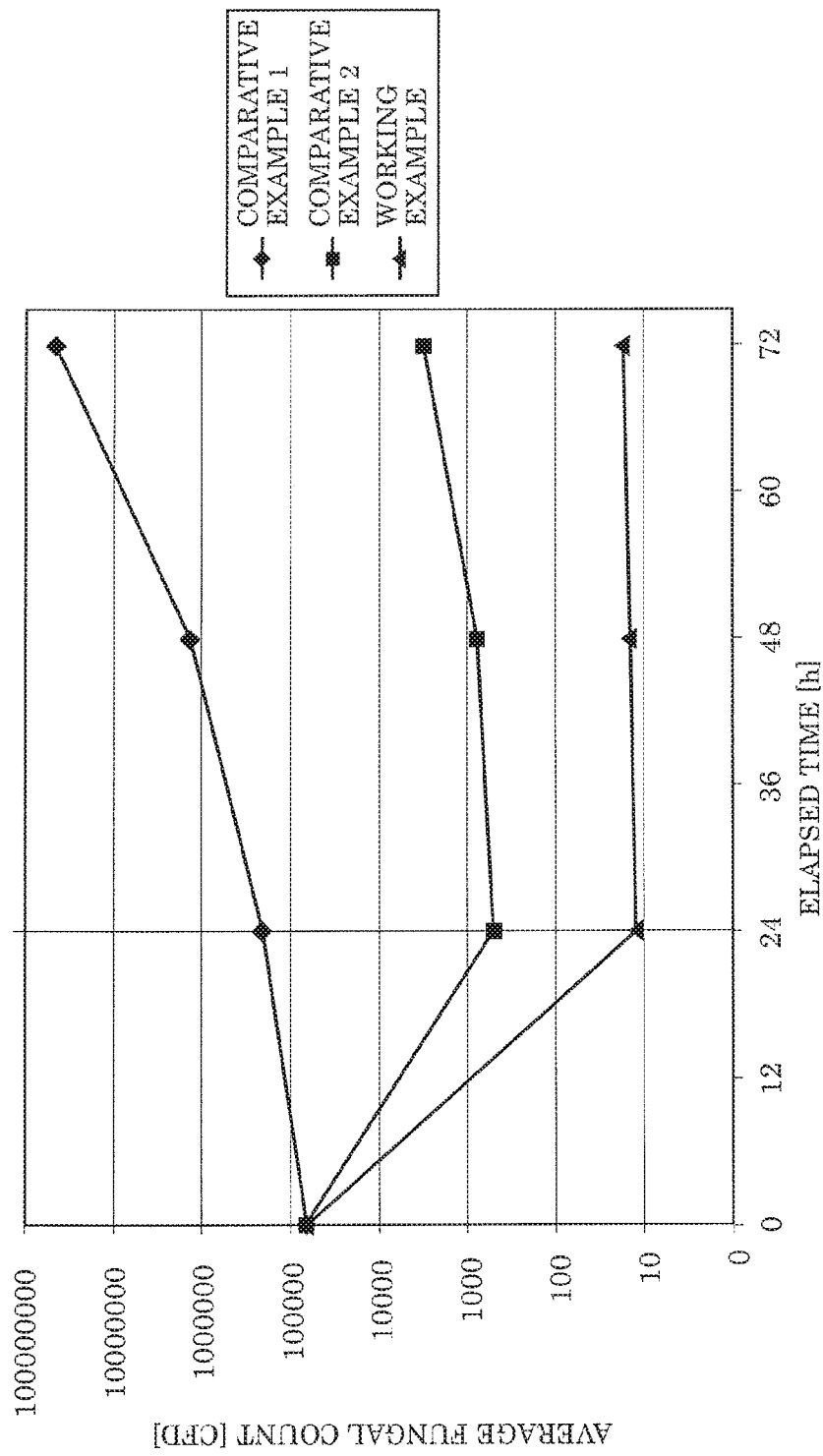

HYPHAE INHIBITION APPARATUS AND HYPHAE INHIBITION METHOD

CROSS REFERENCE TO RELATED APPLICATION

This application claims the benefit of priority of Japanese Patent Application Number 2018-176881 filed on Sep. 21, 2018, the entire content of which is hereby incorporated by reference.

BACKGROUND

1. Technical Field

The present disclosure relates to a hyphae inhibition apparatus and a hyphae inhibition method.

2. Description of the Related Art

Molds appear in wet area facilities such as bathrooms or kitchens or in humid places such as ceiling spaces or under floors. In removing molds, for example, a technique which uses a photocatalyst is known. For example, Japanese Unexamined Patent Application Publication No. 2006-200358 discloses activating a photocatalyst by irradiating the photocatalyst with ultraviolet light to perform disinfecting and deodorizing by photocatalytic reaction.

SUMMARY

However, in the aforementioned conventional technique, proliferation of fungi/bacteria cannot be sufficiently inhibited.

In view of this, the present disclosure provides a hyphae inhibition apparatus and a hyphae inhibition method capable of inhibiting proliferation of organisms with hyphae more efficiently than conventional techniques.

A hyphae inhibition apparatus according to an aspect of the present disclosure is a hyphae inhibition apparatus that irradiates an organism having hyphae with light to inhibit growth of the hyphae, and includes: a first light source generator including at least one of a first light source that emits light having a peak wavelength in a range of from 380 nm to 410 nm, inclusive, or a second light source that emits light having a peak wavelength in a range of from at least 280 nm to below 350 nm; and a second light source generator including at least one of a third light source that emits light having a peak wavelength in a range of from at least 350 nm to below 380 nm or a fourth light source that emits light having a peak wavelength in a range of from 415 nm to 480 nm, inclusive.

Furthermore, a hyphae inhibition method according to an aspect of the present disclosure is a hyphae inhibition method of irradiating an organism having hyphae with light to inhibit growth of the hyphae, and includes: irradiating the organism with at least one of light having a peak wavelength in a range of from 380 nm to 410 nm, inclusive, or light having a peak wavelength in a range of from at least 280 nm to below 350 nm; and irradiating the organism with at least one of light having a peak wavelength in a range of from at least 350 nm to below 380 nm or light having a peak wavelength in a range of from 415 nm to 480 nm, inclusive.

Furthermore, one aspect of the present disclosure can be implemented as a program for causing a computer to execute the above-described hyphae inhibition method. Alternatively, the present disclosure can be implemented as a computer-readable recording medium on which the program is stored.

The present disclosure is capable of inhibiting proliferation of organisms with hyphae more efficiently than conventional techniques.

BRIEF DESCRIPTION OF DRAWINGS

The figures depict one or more implementations in accordance with the present teaching, by way of examples only, not by way of limitations. In the figures, like reference numerals refer to the same or similar elements.

FIG. 6 is a diagram illustrating an example of light irradiation times according to comparative examples 1 and 2 and a working example; and FIG. 7 is a graph illustrating temporal change in average fungal count according to comparative examples 1 and 2 and a working example.

DETAILED DESCRIPTION OF THE EMBODIMENT

Hereinafter, hyphae inhibition apparatuses and a hyphae inhibition method according to exemplary embodiments of the present disclosure will be described in detail with reference to the drawings. It should be noted that each of the subsequently-described exemplary embodiments shows a specific example. Therefore, numerical values, shapes, materials, structural components, the arrangement and connection of the structural components, steps, and the sequence of the steps, etc. shown in the subsequent exemplary embodiments are mere examples, and are not intended to limit the scope of the present disclosure. Furthermore, among the structural components in the subsequent exemplary embodiments, components not recited in any one of the independent claims are described as optional structural components.

Furthermore, the respective figures are schematic diagrams and are not necessarily precise illustrations. Furthermore, in the respective figures, substantially identical components are assigned the same reference signs, and overlapping description thereof is omitted or simplified.

EMBODIMENT

[Configuration]

Figure 1:
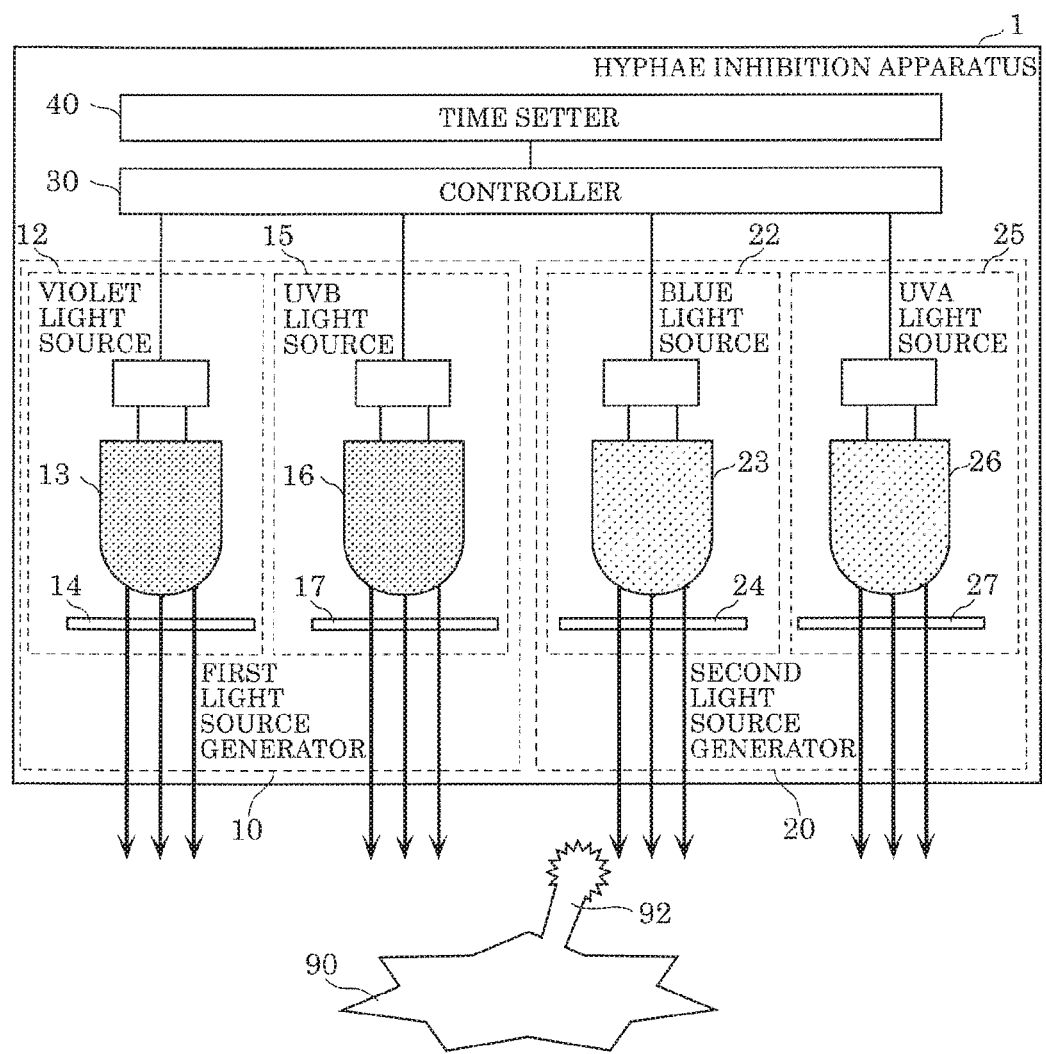
FIG. 1 is a block diagram illustrating a configuration of a hyphae inhibition apparatus according to an embodiment.

First, the configuration of a hyphae inhibition apparatus according to this embodiment will be described with reference to FIG. 1. FIG. 1 is a block diagram illustrating the configuration of hyphae inhibition apparatus 1 according to this embodiment.

As illustrated in FIG. 1, hyphae inhibition apparatus 1 is a hyphae inhibition apparatus that irradiates an organism 90 with hypha 92 with light to thereby inhibit growth of hypha 92. Hyphae inhibition apparatus 1 can inhibit the proliferation of organism 90 by inhibiting the grown of hypha 92 of organism 90.

Organism 90 is what is ordinarily referred to as fungi/bacteria and includes true fungi (eumycetes) such as molds or yeasts, or bacteria such as eubacteria, for example. For example, organism 90 is *cladosporium, rhodotorula*, etc. Specifically, *cladosporium* is any of the *cladosporium* species such as, for example, cladosporioides. Specifically, *rhodotorula* is, for example, any of the *rhodotorula* species. Organism 90 may be *Pseudomonas aeruginosa*.

As illustrated in FIG. 1, hyphae inhibition apparatus 1 includes first light source generator 10 and second light source generator 20. In this embodiment, hyphae inhibition apparatus 1 further includes controller 30 and time setter 40.

As illustrated in FIG. 1, first light source generator 10 includes violet light source 12 and UVB light source 15.

Violet light source 12 is an example of a first light source that emits violet light having a peak wavelength in a range of from 380 nm to 410 nm, inclusive. As illustrated in FIG. 1, violet light source 12 includes light emitting diode (LED) 13 and filter 14.

LED 13 is an example of a light-emitter that emits light including violet light. LED 13 emits, for example, violet monochromatic light.

The violet light emitted by LED 13 has a light emission peak having a full width at half maximum of at most 20 nm. It should be noted that the full width at half maximum may be, for example, at most 15 nm or at most 10 nm. Alternatively, the full width at half maximum may be greater than 20 nm.

The peak wavelength in the light emission peak of the violet light is in a range of from 380 nm to 410 nm, inclusive. It should be noted that the peak wavelength may be in a range of, for example, from 380 nm to 400 nm, inclusive. The peak wavelength is the wavelength at which light emission intensity is highest (or local maximum) in a spectral distribution of violet light.

Figure 2:
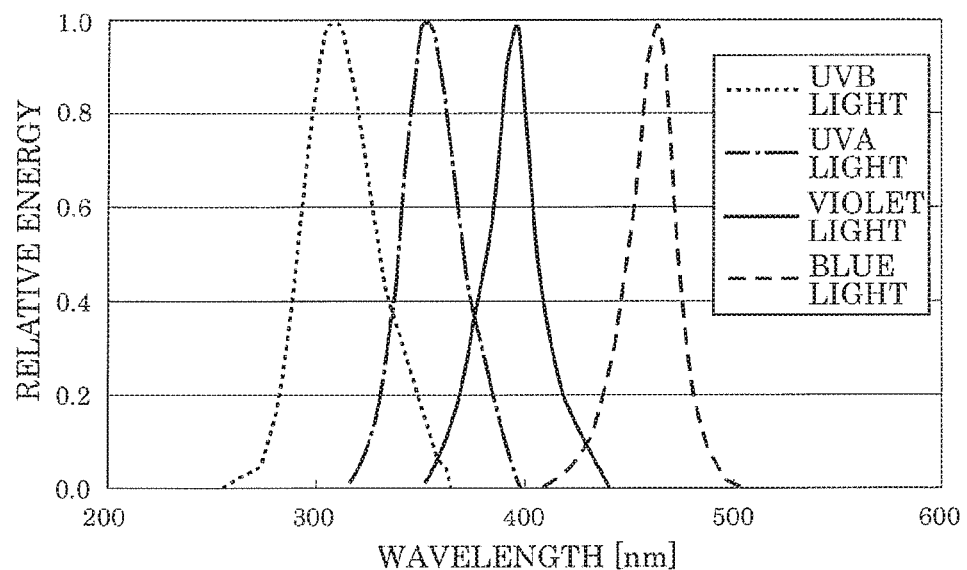
FIG. 2 is a graph illustrating spectra of emitted light of respective light sources included in a hyphae inhibition apparatus according to an embodiment.

LED 13 emits violet light having the light distribution spectrum illustrated in FIG. 2, for example. FIG. 2 is a graph illustrating spectra of emitted light of respective light sources included in hyphae inhibition apparatus 1 according to this embodiment. It should be noted that, in FIG. 2, the horizontal axis represents wavelength and the vertical axis represents relative energy (intensity) of light. As illustrated in FIG. 2, the violet light emitted by LED 13 has a peak wavelength of approximately 391 nm, and a full width at half maximum of approximately 24 nm.

It should be noted that LED 13 may emit light including violet light and another wavelength component, instead of emitting violet monochromatic light. For example, LED 13 may emit visible light including blue light, green light, etc., aside from violet light. For example, LED 13 may emit white light.

Filter 14 transmits only part of the light emitted from LED 13. For example, filter 14 is a band-pass filter that transmits only light having a predetermined wavelength band (transmission band), and sufficiently prevents transmission of light having a wavelength other than the transmission band. The wavelength band of filter 14 ranges from 380 nm to 410 nm, inclusive, for example. With this, it is possible to prevent light having a wavelength below 380 nm and light having a wavelength longer than 410 nm from being included in the light emitted from violet light source 12.

UVB light source 15 is an example of a second light source that emits ultraviolet light (UVB light) having a peak wavelength in a range of from at least 280 nm to below 350 nm. As illustrated in FIG. 1, UVB light source 15 includes LED 16 and filter 17.

LED 16 is an example of a light-emitter that emits light including UVB light. The UVB light emitted by LED 16 has a light emission peak having a full width at half maximum of 38 nm. It should be noted that the full width at half maximum may be, for example, at most 70 nm or at most 10 nm.

The peak wavelength in the light emission peak of the UVB light is in a range of from at least 280 nm to below 350 nm. It should be noted that the peak wavelength may be in a range of from 280 nm to 330 nm, inclusive. The peak wavelength is the wavelength at which light emission intensity is highest (or local maximum) in a spectral distribution of UVB light.

LED 16 emits UVB light having the light distribution spectrum illustrated in FIG. 2, for example. As illustrated in FIG. 2, the UVB light emitted by LED 16 has a peak wavelength of approximately 315 nm, and a full width at half maximum of approximately 38 nm.

It should be noted that LED 16 may emit light including UVB light and another wavelength component. For example, LED 16 may emit light including ultraviolet light having a wavelength below 280 nm, and so on.

Filter 17 transmits only part of the light emitted from LED 16. For example, filter 17 is a band-pass filter that transmits only light of a predetermined wavelength band (transmission band), and sufficiently prevents transmission of light of a wavelength other than the transmission band. The wavelength band of filter 17 ranges from at least 280 nm to below 350 nm, for example. With this, it is possible to prevent light having a wavelength below 280 nm and light having a wavelength longer than 350 nm from being included in the light emitted from UVB light source 15.

The light that is emitted when first light source generator 10 emits light is violet light having a wavelength in a range of from 380 nm to 410 nm, inclusive, or UVB light having a wavelength in a range of from at least 280 nm to below 350 nm, or a mixed light thereof, and any of these lights can inhibit the growth of hypha 92. Specifically, the violet light is light having a function of weakening hypha 92. Furthermore, the UVB light is light having a function of breaking down hypha 92.

As illustrated in FIG. 1, second light source generator 20 includes blue light source 22 and UVA light source 25. Blue light source 22 is an example of a fourth light source that emits blue light having a peak wavelength in a range of from 415 nm to 480 nm, inclusive. As illustrated in FIG. 1, blue light source 22 includes LED 23 and filter 24.

LED 23 is an example of a light-emitter that emits light including blue light. LED 23 emits, for example, blue monochromatic light.

The blue light emitted by LED 23 has a light emission peak having a full width at half maximum of 25 nm. It should be noted that the full width at half maximum may be, for example, at most 70 nm or at most 10 nm.

The peak wavelength in the light emission peak of the blue light is in a range of from 415 nm to 480 nm, inclusive. It should be noted that the peak wavelength may be in a range of from 430 nm to 470 nm, inclusive. The peak wavelength is the wavelength at which light emission intensity is highest (or local maximum) in a spectral distribution of blue light.

LED 23 emits blue light having the light distribution spectrum illustrated in FIG. 2, for example. As illustrated in FIG. 2, the blue light emitted by LED 23 has a peak wavelength of approximately 470 nm, and a full width at half maximum of approximately 24 nm.

It should be noted that LED 23 may emit light including blue light and another wavelength component, instead of emitting blue monochromatic light. For example, LED 23 may emit visible light including green light, etc., aside from blue light. For example, LED 23 may emit white light.

Filter 24 transmits only part of the light emitted from LED 23. For example, filter 24 is a band-pass filter that transmits only light of a predetermined wavelength band (transmission band), and sufficiently prevents transmission of light of a wavelength other than the transmission band. The wavelength band of filter 24 ranges from 415 nm to 480 nm, inclusive, for example. With this, it is possible to prevent light having a wavelength below 415 nm and light having a wavelength longer than 480 nm from being included in the light emitted from blue light source 22.

UVA light source 25 is an example of a third light source that emits ultraviolet light (UVA light) having a peak wavelength in a range of from at least 350 nm to below 380 nm. As illustrated in FIG. 1, UVA light source 25 includes LED 26 and filter 27.

LED 26 is an example of a light-emitter that emits light including UVA light. The UVA light emitted by LED 26 has a light emission peak having a full width at half maximum of 33 nm. It should be noted that the full width at half maximum may be, for example, at most 50 nm or at most 10 nm.

The peak wavelength in the light emission peak of the UVA light is in a range of from at least 350 nm to below 380 nm. The peak wavelength is the wavelength at which light emission intensity is highest (or local maximum) in a spectral distribution of UVA light.

LED 26 emits UVA light having the light distribution spectrum illustrated in FIG. 2, for example. As illustrated in FIG. 2, the UVA light emitted by LED 26 has a peak wavelength of approximately 365 nm, and a full width at half maximum of approximately 33 nm.

It should be noted that LED 26 may emit light including UVA light and another wavelength component. For example, LED) 26 may emit light including ultraviolet light having a wavelength below 350 nm, and so on.

Filter 27 transmits only part of the light emitted from LED 26. For example, filter 27 is a band-pass filter that transmits only light of a predetermined wavelength band (transmission band), and sufficiently prevents transmission of light of a wavelength other than the transmission band. The wavelength band of filter 27 ranges from at least 350 nm to below 380 nm, for example. With this, it is possible to prevent light having a wavelength below 350 nm and light having a wavelength longer than 380 nm from being included in the light emitted from UVA light source 25.

The light that is emitted when second light source generator 20 emits light is blue light having a wavelength in a range of from 415 nm to 480 nm, inclusive, or UVA light having a wavelength in a range of from at least 350 nm to below 380 nm, or a mixed light thereof, and these lights can promote the growth of hypha 92. Specifically, each of the blue light and the UVA light has a function of causing hypha 92 of organism 90 to grow long and thin.

Controller 30 controls the light emission and the stopping of light emission of first light source generator 10 and second light source generator 20. Specifically, controller 30 controls the light emission time, the light emission start and end timing, and the light emission method (i.e., the light irradiation range, and so on) of each of first light source generator 10 and second light source generator 20. For example, controller 30 causes first light source generator 10 and second light source generator 20 to emit light by supplying power supplied from an external power source or a battery, etc., to first light source generator 10 and second light source generator 20.

Control circuit 30 is, for example, a microcontroller. Controller 30 is, for example, implemented by a non-volatile memory in which a program is stored, a volatile memory which is a transitory storage region for executing the program, an input/output port, a processor that executes the program, and so on. The function of controller 30 may be implemented by software executed by a processor, or may be implemented by hardware such as an electronic circuit including a plurality of circuit elements.

In this embodiment, controller 30 causes first light source generator 10 to emit light after causing second light source generator 20 to emit light. Controller 30 may cause second light source generator 20 to emit light after causing first light source generator 10 to emit light. For example, controller repeats alternately causing first light source generator 10 to emit light and causing second light source generator 20 to emit light. Controller 30 causes second light source generator 20 to stop emitting light during a period in which controller 30 is causing first light source generator 10 to emit light. Controller causes first light source generator 10 to stop emitting light during a period in which controller 30 is causing second light source generator 20 to emit light. In other words, controller 30 causes mutually-exclusive light emission of first light source generator 10 and second light source generator 20.

For example, controller 30 controls first light source generator 10 and second light source generator 20 so that the irradiation integrated quantity of light from second light source generator 20 is less than or equal to the irradiation integrated quantity of light from first light source generator 10. Furthermore, for example, controller 30 controls first light source generator 10 and second light source generator 20 so that the irradiation integrated quantity of light from second light source generator 20 is less than or equal to half or less than or equal to one-fourth the irradiation integrated quantity of light from first light source generator 10. Irradiation integrated quantity represents the product of irradiation amount per unit time and irradiation time.

In this embodiment, controller 30 controls first light source generator and second light source generator 20 so that the irradiation time of light from second light source generator 20 is shorter than or equal to the irradiation time of light from first light source generator 10. Furthermore, for example, controller 30 controls first light source generator 10 and second light source generator 20 so that the irradiation time of light from second light source generator 20 is shorter than or equal to half or shorter than or equal to one-fourth the irradiation time of light from first light source generator 10. Specifically, controller 30 controls first light source generator 10 and second light source generator 20 based on time information set by time setter 40.

It should be noted that violet light source 12 and UVB light source 15 are caused to emit light at the same time within the irradiation period of light from first light source generator 10, but may be caused to emit light at mutually-exclusive times. At this time, for example, the light emission time of violet light source 12 may be longer than or equal to the light emission time of UVB light source 15. Moreover, blue light source 22 and UVA light source 25 are caused to emit light at the same time within the irradiation period of light from second light source generator 20, but may be caused to emit light at mutually-exclusive times. At this time, for example, the light emission time of blue light source 22 may be longer than or equal to the light emission time of UVA light source 25.

Furthermore, controller 30 may control first light source generator 10 and second light source generator 20 so that the irradiation energy of light from second light source generator 20 is less than or equal to the irradiation energy of light from first light source generator 10. In other words, controller 30 may control first light source generator 10 and second light source generator 20 so that the irradiation energy of light that inhibits growth of hypha 92 is less than or equal to the irradiation energy of light that promotes growth of hypha 92. Furthermore, for example, controller 30 controls first light source generator 10 and second light source generator 20 so that the irradiation energy of light from second light source generator 20 is less than or equal to half or less than or equal to one-fourth the irradiation energy of light from first light source generator 10.

Time setter 40 sets the irradiation times of first light source generator and second light source generator 20. Time setter 40 sets the irradiation times of first light source generator 10 and second light source generator 20 based on an instruction from a user, predetermined schedule information, or the like. Schedule information is, for example, information indicating the timing for starting and the timing for ending irradiation of light.

Although not illustrated in the figures, an operating switch for starting and stopping the irradiation of light may be provided in hyphae inhibition apparatus 1. Furthermore, hyphae inhibition apparatus 1 may include a battery, or may include an outlet plug for receiving power from an external power source, or the like.

Figure 3:
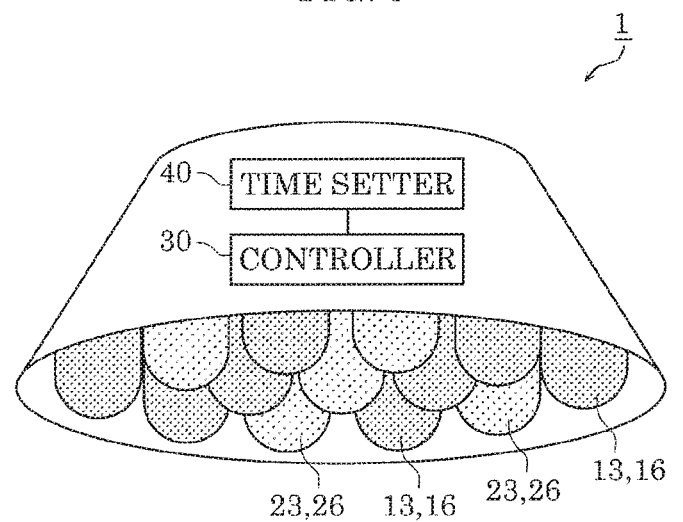
FIG. 3 is a schematic perspective view of a hyphae inhibition apparatus according to an embodiment.

FIG. 3 is a schematic perspective view of hyphae inhibition apparatus 1 according to this embodiment. In FIG. 3, fine dot meshing is provided on LEDs 13 and 16 included in first light source generator 10, and course dot meshing is provided on LEDs 23 and 26 included in second light source generator 20. It should be noted that illustration of the respective filters is omitted in FIG. 3. The amount of light from each LED is, for example, the same, but may be different.

As illustrated in FIG. 3, a plurality of LEDs 13, 16, 23, and 26 are dispersed in a plane in hyphae inhibition apparatus 1. For example, hyphae inhibition apparatus 1 is configured so that the irradiation range of the violet light emitted when only the plurality of LEDs 13 emit light, the irradiation range of the UVB light emitted when only the plurality of LEDs 16 emit light, the irradiation range of the blue light emitted when only the plurality of LEDs 23 emit light, and the irradiation range of the UVA light emitted when only the plurality of LEDs 26 emit light are mutually the same.

In this embodiment, the number of LEDs 13 or 16 included in first light source generator 10 is larger than the number of LEDs 23 or 26 included in second light source generator 20. Specifically, LEDs 13 which emit violet light are greatest in number, followed in descending order by LEDs 16 which emit UVB light, LEDs 23 which emit blue light, and LEDs 26 which emit UVA light. Accordingly, the irradiation energy of violet light is greatest, followed in descending order by UVB light, blue light, and UVA light.

Here, the magnitude of the output of the respective LEDs is the same but may be different. Furthermore, for example, the number of the respective LEDs may be mutually the same. In this case, the output of LEDs 13 which emit violet light may be highest, followed in descending order by LEDs 16 which emit UVB light, LEDs 23 which emit blue light, and LEDs 26 which emit UVA light.

Furthermore, in this embodiment, an example is given in which hyphae inhibition apparatus 1 includes the four light sources, namely, violet light source 12, UVB light source 15, blue light source 22, and UVA light source 25, but the configuration is not limited to such. Hyphae inhibition apparatus 1 may include at least one of violet light source 12 and UVB light source 15, and at least one of blue light source 22 and UVA light source 25.

Figure 4:
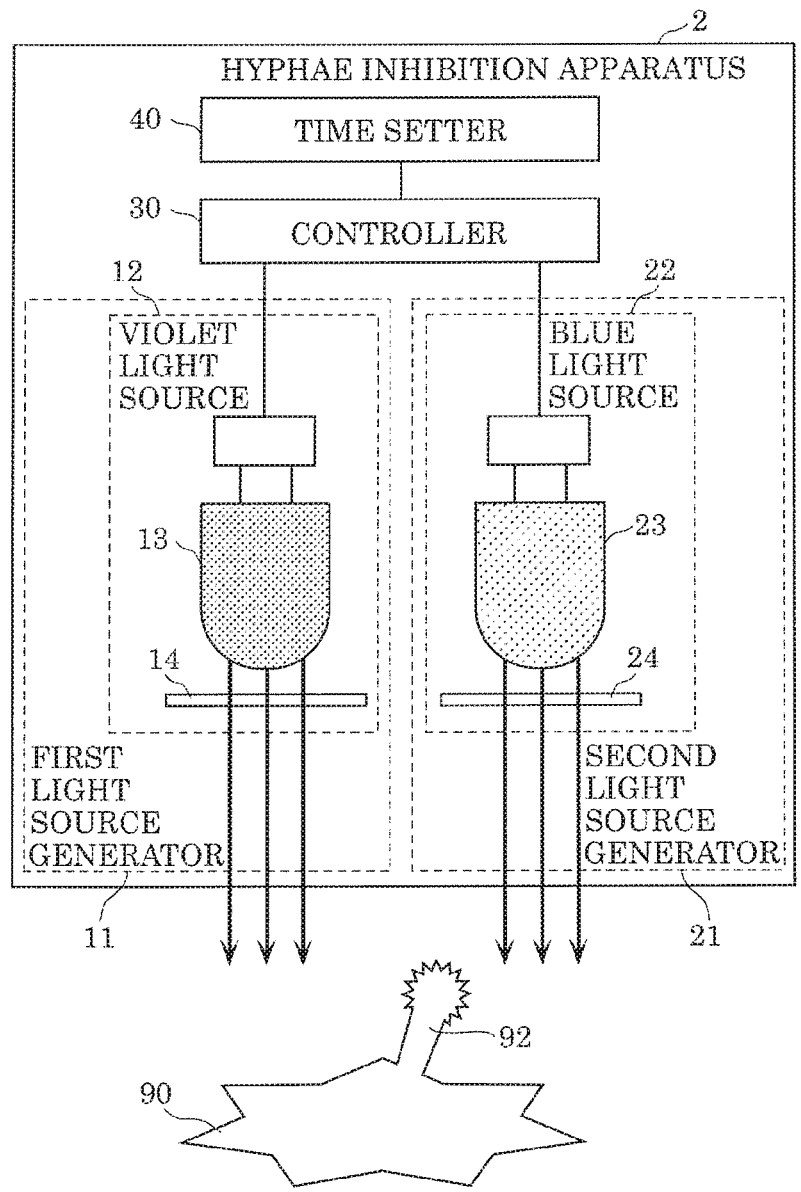
FIG. 4 is a block diagram illustrating another configuration of a hyphae inhibition apparatus according to an embodiment.

FIG. 4 is a block diagram illustrating another configuration of a hyphae inhibition apparatus according to this embodiment. Compared to hyphae inhibition apparatus 1 illustrated in FIG. 1, hyphae inhibition apparatus 2 illustrated in FIG. 4 is different in including first light source generator 11 and second light source generator 21 in place of first light source generator 10 and second light source generator 20.

First light source generator 11 includes only violet light source 12. In other words, first light source generator 11 does not include UVB light source 15.

Second light source generator 21 includes only blue light source 22. In other words, second light source generator 21 does not include UVA light source 25.

In this manner, hyphae inhibition apparatus 2 includes only light sources that emit visible light, and does not include a light source that emits ultraviolet light. For this reason, the inhibition of hypha 92 can be performed even when a component formed using a resin material, and the like, which is easily affected by ultraviolet light, is included in the light irradiation range. In other words, hyphae inhibition apparatus 2 is implemented as a hyphae inhibition apparatus having few usage environment restrictions and high versatility.

[Operation]

Figure 5:
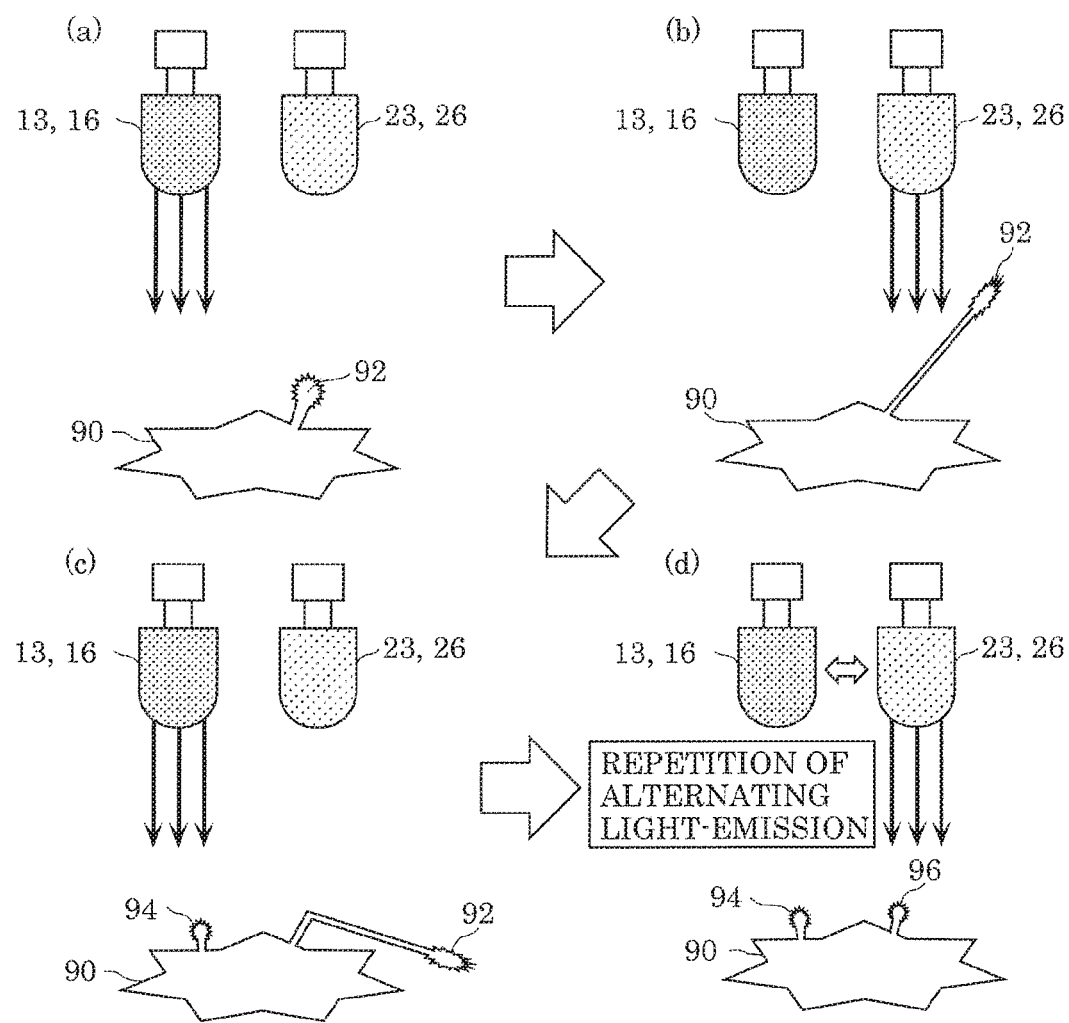
FIG. 5 is a diagram illustrating operation of a hyphae inhibition apparatus according to an embodiment and behavior of hyphae of an organism.

Next, the operation of above-described hyphae inhibition apparatus 1 will be described with reference to FIG. 5. FIG. 5 is a diagram illustrating the operation of hyphae inhibition apparatus 1 according to this embodiment and the behavior of hypha 92 of organism 90. It should be noted that the operation of hyphae inhibition apparatus 2 is the same as the operation of hyphae inhibition apparatus 1, and thus description will be omitted.

First, as illustrated in (a) in FIG. 5, organism 90 is irradiated with the light from first light source generator 10. Specifically, controller 30 supplies power to LEDs 13 and 16 included in first light source 10 to thereby cause LEDs 13 and 16 to emit light and irradiate organism 90 with the violet light and the UVB light from LEDs 13 and 16. It should be noted that, in the case of hyphae inhibition apparatus 2, organism 90 is irradiated only with the violet light from LED 13. With the irradiation with the violet light and the UVB light, growth of hypha 92 is inhibited.

Next, as illustrated in (b) in FIG. 5, organism 90 is irradiated with the light from second light source generator 20. At this time, irradiation with the light from first light source generator 10 is stopped. Specifically, controller 30 supplies power to LEDs 23 and 26 included in second light source 20 to thereby cause LEDs 23 and 26 to emit light and irradiate organism 90 with the blue light and the UVA light from LEDs 23 and 26. At this time, controller 30 stops the supply of power to LEDs 13 and 16 included in first light source 10 such that organism 90 is not irradiated with the violet light and the UVB light from LEDs 13 and 16. It should be noted that, in the case of hyphae inhibition apparatus 2, organism 90 is irradiated only with the blue light from LED 23.

With the irradiation with the blue light and the UVA light, growth of hypha 92 is promoted. Specifically, as illustrated in (b) of FIG. 5, hypha 92 grows long and thin. Hypha 92 which has grown long and thin becomes weak and easy to destroy.

Next, as illustrated in (c) in FIG. 5, organism 90 is irradiated with the light from first light source generator 10. The specific process is the same as in (a) in FIG. 5. By irradiation with violet light and UVB light, hypha 92 which has grown long further weakens or is destroyed. Furthermore, at this time growth of new hypha 94 is inhibited. The weakened hypha 92 stops growing further and is eventually destroyed.

Hereinafter, as illustrated in (d) in FIG. 5, irradiation with the light from second light source generator 20 and irradiation with light from the first light source generator 10 is repeated. As a result of the repetition, growth of new hyphae 94 and 96 is inhibited.

[Test Results]

Next, results of a test that was actually performed to verify the effects of hyphae inhibition apparatus 1 or 2 according to this embodiment will be described.

*Rhodotorula* was used as test fungi/bacteria which is an example of organism 90 that serves as the subject. Specifically, after adjusting the fungi density to approximately $10^4$ CFU/mL, test fungi/bacteria were exposed under the respective conditions of comparative example 1, comparative example 2, and a working example as illustrated in FIG. 6. Subsequently, culturing is performed for three days, and the fungal count was taken.

FIG. 6 is a diagram illustrating an example of light irradiation times according to comparative examples 1 and 2 and the working example. In FIG. 6, (a) to (c) illustrate respective light irradiation conditions of comparative examples 1 and 2 and the working example. In each of (a) to (c) in FIG. 6, the horizontal axis shows time.

As illustrated in (a) in FIG. 6, in comparative example 1, the test fungi/bacteria was left to rest in darkness for 24 hours. As illustrated in (b) in FIG. 6, in comparative example 2, the test fungi/bacteria were irradiated for 24 hours with violet light having an irradiation intensity of 500 $\mu$W/cm$^2$ and a peak wavelength of 391 nm. As illustrated in (c) in FIG. 6, in the working example, irradiation with violet light having an irradiation intensity of 500 $\mu$W/cm$^2$ and a peak wavelength of 391 nm and irradiation of blue light having an irradiation intensity of 500 $\mu$W/cm$^2$ and a peak wavelength of 470 nm was alternatingly repeated. The irradiation time of the violet light was two hours and the irradiation time of the blue light was 1 hour, and each was performed for eight repetitions to thereby perform irradiation for a total of twenty-four hours.

FIG. 7 is a graph illustrating temporal change in average fungal count according to comparative examples 1 and 2 and the working example. In FIG. 7, the horizontal axis represents elapsed time, and the vertical axis represents the average fungal count. The time up to when the elapsed time reaches 24 hours is equivalent to the irradiation time of light illustrated in (b) and (c) in FIG. 6. The elapsed time from 24 hours onward is the subsequent rest time. From 24 hours onward, the test fungi/bacteria were left to rest in darkness in all of comparative examples 1 and 2 and the working example.

As illustrated in FIG. 7, in comparative example 1 the fungal count increased with the passage of time. In comparative example 2 and the working example, the fungal count decreased in both at the point in time when light irradiation was stopped (that is, at the point in time when 24 hours elapsed). At this time, there was a more than one-digit reduction in fungal count of the working example compared to that of comparative example 2. In other words, it can be understood that the working example has a higher fungi/bacteria inhibiting effect compared to comparative example 2. A possible factor for this is that, with violet light irradiation only, the fungi are able to adjust to the violet light and thus the inhibiting effect of violet light weakened.

Furthermore, even after light irradiation was stopped (that is, from 24 hours onward), there was practically no increase in the fungal count for the working example, whereas the fungal count increased gradually for comparative example 2. In this manner, according to this embodiment, proliferation of fungi/bacteria after light irradiation is stopped can also be inhibited. Therefore, since it is possible to secure a long interval (non-irradiation period) until the next light irradiation, energy conservation also becomes possible.

Advantageous Effects, Etc.

As described above, hyphae inhibition apparatus 1 or 2 according to this embodiment, is a hyphae inhibition apparatus that irradiates organism 90 with hypha 92 with light to inhibit growth of hypha 92, and includes first light source generator 10 or 11 including at least one of violet light source 12 that emits light having a peak wavelength in a range of from 380 nm to 410 nm, inclusive, or UVB light source 15 that emits light having a peak wavelength in a range of from at least 280 nm to below 350 nm; and second light source generator 20 or 21 including at least one of UVA light source 25 that emits light having a peak wavelength in a range of from at least 350 nm to below 380 nm or blue light source 22 that emits light having a peak wavelength in a range of from 415 nm to 480 nm, inclusive.

Accordingly, growth of hypha 92 can be inhibited by the light from first light source generator 10 or 11, and growth of hypha 92 is promoted by the light from second light source generator 20 or 21. By irradiation with light having the two functions of inhibiting and promoting the growth of hypha 92, hypha 92 does not easily develop resistance, and thus proliferation of organism 90 with hypha 92 can be more efficiently inhibited than in the conventional techniques.

Furthermore, for example, hyphae inhibition apparatus 1 or 2 further includes controller 30 that causes first light source generator 10 or 11 to emit light, after causing second light source generator 20 or 21 to emit light.

Accordingly, when organism 90 is irradiated with the light from second light source generator 20 or 21 which promotes the growth of hypha 92, hypha 92 grows long and thin and weakens. Irradiating the weakened and extended hypha 92 with the light from first light source generator 10 or 11 for inhibiting the growth of hypha 92 makes hypha 92 easy to destroy. Accordingly, proliferation of organism 90 with hypha 92 can be inhibited more efficiently than in the conventional techniques.

Furthermore, for example, controller 30 causes second light source generator 20 or 21 to stop emitting light during a period in which controller 30 is causing first light source generator 10 or 11 to emit light, and causes first light source generator 10 or 11 to stop emitting light during a period in which controller 30 is causing second light source generator 20 or 21 to emit light.

Accordingly, by separating promotion and inhibition of growth of hypha 92, the inhibiting effect can be further enhanced.

For example, controller 30 repeats alternately causing light emission by first light source generator 10 or 11 and causing light emission by second light source generator 20 or 21.

Accordingly, proliferation of organism 90 with hypha 92 can be more efficiently inhibited.

Furthermore, for example, first light source generator 10 includes violet light source 12 and UVB light source 15. Second light source generator 20 includes UVA light source 25 and blue light source 22.

Accordingly, since hypha 92 can be destroyed by using ultraviolet light, proliferation of organism 90 can be more efficiently inhibited.

Furthermore, for example, first light source generator 11 includes only violet light source 12 out of violet light source 12 and UVB light source 15. Second light source generator 21 includes only blue light source 22 out of UVA light source 25 and blue light source 22.

Accordingly, hyphae inhibition apparatus 2 does not include a light source that emits ultraviolet light, and thus can be used to inhibit growth of organism 90 which has attached itself to or is located near a component that is formed using a resin material that is easily affected by ultraviolet light. In this manner, compared to when a light source for ultraviolet light is included, there are not restrictions on the environment in which it is usable, and thus versatility of inhibition apparatus 2 can be enhanced.

Furthermore, for example, the irradiation energy of the light emitted by second light source generator 20 or 21 is lower than or equal to the irradiation energy of the light emitted by first light source generator 10 or 11.

Accordingly, since hypha 92 which has grown long and thin can sufficiently be weakened, proliferation of organism 90 can be more efficiently inhibited.

Furthermore, for example, the irradiation integrated quantity of the light emitted by second light source generator 20 or 21 is less than or equal to the irradiation integrated quantity of the light emitted by first light source generator 10 or 11.

Accordingly, since hypha 92 which has grown long and thin can sufficiently be weakened, proliferation of organism 90 can be more efficiently inhibited.

Furthermore, for example, the irradiation time of the light emitted by second light source generator 20 or 21 is shorter than or equal to the irradiation time of the light emitted by first light source generator 10 or 11.

Accordingly, since hypha 92 which has grown long and thin can sufficiently be weakened, proliferation of organism 90 can be more efficiently inhibited.

Furthermore, for example, organism 90 is one of *cladosporium* and *rhodotorula*.

Accordingly, it is possible to effectively inhibit the growth of *cladosporium, rhodotorula*, etc., which tend to appear in wet area facilities such as bathrooms or kitchens or in humid places such as in ceiling spaces or under floors.

Furthermore, for example, organism 90 may be *Pseudomonas aeruginosa*.

When a person with compromised immunity is exposed to *Pseudomonas aeruginosa*, there is the risk of contracting *Pseudomonas aeruginosa* infection. Hyphae inhibition apparatus 1 or 2 inhibits the growth of *Pseudomonas aeruginosa*, and thus can be useful in disease prevention.

Furthermore, for example, a hyphae inhibition method according to this embodiment is a hyphae inhibition method of irradiating organism 90 having hypha 92 with light to inhibit growth of hypha 92, and includes: irradiating organism 90 with at least one of light having a peak wavelength in a range of from 380 nm to 410 nm, inclusive, or light having a peak wavelength in a range of from at least 280 nm to below 350 nm; and irradiating organism 90 with at least one of light having a peak wavelength in a range of from at least 350 nm to below 380 nm or light having a peak wavelength in a range of from 415 nm to 480 nm, inclusive.

Accordingly, proliferation of organism 90 with hypha 92 can be inhibited more efficiently than in the conventional techniques, in the same manner as above-described hyphae inhibition apparatus 1 or 2.

(Others)

Although hyphae inhibition apparatuses according to the present disclosure are described based on the foregoing exemplary embodiment, the present disclosure is not limited to the foregoing exemplary embodiment.

For example, organism 90 with hypha 92 is exemplified as *cladosporium, rhodotorula*, and *Pseudomonas aeruginosa* in the foregoing exemplary embodiment, but is not limited to such. For example, organism 90 may be filamentous fungi, and the like, which cause powdery mildew, blast disease, etc.

Furthermore, since hyphae inhibition apparatus 1 or 2 and the hyphae inhibition method according to the foregoing embodiment is capable of inhibiting the appearance of molds and yeasts, the appearance of insect pests that feed on molds and yeasts can also be inhibited. For example, the appearance of psocids which feed on molds and yeasts can be inhibited. With this, the appearance of cheyletids which feed on the psocids can additionally be inhibited.

In this manner, by inhibiting the appearance of fungi/bacteria such as molds and yeasts, appearance of insect pests that do harm to the human body can be inhibited. In other words, hyphae inhibition apparatus 1 or 2 and the hyphae inhibition method according to the foregoing embodiment also indirectly have insect pest expelling and controlling effects.

Furthermore, for example, a photocatalyst may be disposed in advance inside the irradiation range of light from hyphae inhibition apparatus 1 or 2. Irradiating the photocatalyst with the light from hyphae inhibition apparatus 1 or 2 activates the photocatalyst, thereby enabling promotion of decomposition of hypha 92.

Furthermore, for example, in the foregoing embodiment, hyphae inhibition apparatus 1 or 2 is exemplified as including LEDs and a filter for each type of light, but may include a single light source (LED) and two or more filters. Specifically, a single light source may be shared between the first light source generator and the second light source generator. For example, by mechanically switching filters through which light emitted from one light source passes, two types of light may be emitted. Alternatively, two types of light may be emitted by providing, in the light entrance side or light exit side of a filter, a light-blocking wall that can open and close and switching between opening and closing the light-blocking wall.

Furthermore, for example, the light emission by first light source generator 10 and the light emission by second light source generator 20 may be performed simultaneously. For example, controller 30 may cause second light source generator 20 to emit light while first light source generator 10 is emitting light, and then subsequently cause first light source generator 10 to stop emitting light. In the same manner, controller 30 may cause first light source generator 10 to emit light while second light source generator 20 is emitting light, and then subsequently cause second light source generator 20 to stop emitting light. In this manner, the light emission by first light source generator 10 and the light emission by second light source generator 20 need not be fully performed temporally mutually exclusively, and may be formed with parts of the respective light emission periods overlapping.

Furthermore, for example, hyphae inhibition apparatus 1 or 2 is used by being attached to the drainage port of a bathroom, or the like, but is not limited to such. Hyphae inhibition apparatus 1 or 2 can be applied in all environments that can come into contact with water or vapor.

For example, hyphae inhibition apparatus 1 or 2 can be used in ordinary homes such as a house. Specifically, hyphae inhibition apparatus 1 or 2 may be installed in wet area facilities such as toilets, kitchens, wash basins, drain pipes, etc. Alternately, hyphae inhibition apparatus 1 or 2 may be installed in locations where condensation tends to occur such as under floors, in ceiling spaces, window sashes, etc. Furthermore, hyphae inhibition apparatus 1 or 2 may be installed in poorly ventilated shoe cabinets, clothes chests, closets, etc.

Furthermore, for example, hyphae inhibition apparatus 1 or 2 may be installed in electrical appliances. Specifically, hyphae inhibition apparatus 1 or 2 may be installed in dishwashers, washing machines, refrigerators, rice cookers, alkali ion water purifiers, vacuum cleaners, or air conditioning equipment such as ventilating fans, dehumidifiers, driers, humidifiers, etc.

Furthermore, for example, hyphae inhibition apparatus 1 or 2 can also be used in the fields of agriculture, fishery, and livestock. Specifically, hyphae inhibition apparatus 1 or 2 may be installed in plastic greenhouses, food processing plants, slaughterhouses, fish delivery centers, wholesale markets, etc. For example, food processing plants include processing plants for various food products such as canned goods, cut vegetables, powdered foodstuff, liquor, frozen food, etc. Furthermore, hyphae inhibition apparatus 1 or 2 can be used in plant factories using artificial light, in protected horticulture using both artificial light and sunlight, as outdoor lamps for outdoor cultivation, etc.

Furthermore, for example, hyphae inhibition apparatus 1 or 2 can also be used in the industrial field. For example, hyphae inhibition apparatus 1 or 2 may be installed in drainage equipment, etc., of semiconductor wafer manufacturing plants, etc.

Furthermore, for example, hyphae inhibition apparatus 1 or 2 can be installed in the various edifices of various institutions such as office buildings, hospitals, nursing homes, supply centers for school meals, schools, etc. Furthermore, for example, hyphae inhibition apparatus 1 or 2 may be installed in eating establishments such as cafes, restaurants, bars, etc., or stores of retailers such as flower shops, pet shops, etc. Furthermore, for example, hyphae inhibition apparatus 1 or 2 may be installed in the food sections of supermarkets or department stores. Specifically, hyphae inhibition apparatus 1 or 2 may be used near the fresh fish corner or refrigeration facilities including the ceiling.

Furthermore, in the foregoing embodiment, structural components such as controller 30 and time setter 40 may be configured using dedicated hardware or may be implemented by executing software programs suitable for the respective structural components. Each of the structural components may be implemented by a program executing component, such as a central processing unit (CPU) or processor, reading and executing a software program recorded on a recording medium such as a hard disc or a semiconductor memory.

It should be noted that the present disclosure can be implemented not only as a hyphae inhibition apparatus but also as a program which includes, as steps, the processes performed by the respective structural components of the hyphae inhibition apparatus, and a computer-readable recording medium on which such program is recorded, such as a digital versatile disc (DVD), etc.

Specifically, the above-described generic or specific aspects may be implemented as a system, an apparatus, an integrated circuit, a computer program, and a computer-readable recording medium, and may be implemented by an arbitrary combination of a system, an apparatus, an integrated circuit, a computer program, and a recording medium.

Forms obtained by various modifications to the exemplary embodiments that can be conceived by a person of skill in the art as well as forms realized by arbitrarily combining structural components and functions in the exemplary embodiments which are within the scope of the essence of the present disclosure are included in the present disclosure.

What is claimed is:

1. A hyphae inhibition apparatus that irradiates an organism having hyphae with light to inhibit growth of the hyphae, the hyphae inhibition apparatus comprising:
    a first light source generator including at least one of a first light source that emits light having a peak wavelength in a range of from 380 nm to 410 nm, inclusive, or a second light source that emits light having a peak wavelength in a range of from at least 280 nm to below 350 nm;
    a second light source generator including at least one of a third light source that emits light having a peak wavelength in a range of from at least 350 nm to below 380 nm or a fourth light source that emits light having a peak wavelength in a range of from 415 nm to 480 nm, inclusive; and
    a controller that causes the first light source generator to emit light, after causing the second light source generator to emit light,
    wherein the controller causes the second light source generator to stop emitting light during a period in which the controller is causing the first light source generator to emit light, and causes the first light source generator to stop emitting light during a period in which the controller is causing the second light source generator to emit light.

2. The hyphae inhibition apparatus according to claim 1, wherein the controller repeats alternately causing light emission by the first light source generator and light emission by the second light source generator.

3. The hyphae inhibition apparatus according to claim 1, wherein the first light source generator includes the first light source and the second light source, and
    the second light source generator includes the third light source and the fourth light source.

4. The hyphae inhibition apparatus according to claim 1, wherein the first light source generator includes only the first light source out of the first light source and the second light source, and
    the second light source generator includes only the fourth light source out of the third light source and the fourth light source.

5. The hyphae inhibition apparatus according to claim 1, wherein an irradiation intensity of light emitted by the second light source generator is lower than or equal to an irradiation intensity of light emitted by the first light source generator.

6. The hyphae inhibition apparatus according to claim 1, wherein an irradiation integrated quantity of light emitted by the second light source generator is less than or equal to an irradiation integrated quantity of light emitted by the first light source generator.

7. The hyphae inhibition apparatus according to claim 1, wherein an irradiation time of light emitted by the second light source generator is shorter than or equal to an irradiation time of the light emitted by first light source generator.

8. The hyphae inhibition apparatus according to claim 1, wherein the organism is one of *cladosporium* and *rhodotorula*.

9. The hyphae inhibition apparatus according to claim 1, wherein the organism is *Pseudomonas aeruginosa*.

10. A hyphae inhibition method of irradiating an organism having hyphae with light to inhibit growth of the hyphae, the hyphae inhibition method comprising:

irradiating, by a first light source generator, the organism with at least one of light having a peak wavelength in a range of from 380 nm to 410 nm, inclusive, or light having a peak wavelength in a range of from at least 280 nm to below 350 nm;

irradiating, by a second light source generator, the organism with at least one of light having a peak wavelength in a range of from at least 350 nm to below 380 nm or light having a peak wavelength in a range of from 415 nm to 480 nm, inclusive; and causing, by a controller, the first light source generator to emit light, after causing the second light source generator to emit light, wherein the controller causes the second light source generator to stop emitting light during a period in which the controller is causing the first light source generator to emit light, and causes the first light source generator to stop emitting light during a period in which the controller is causing the second light source generator to emit light.

\* \* \* \* \*